US010232179B2

(12) United States Patent
Grill et al.

(10) Patent No.: US 10,232,179 B2
(45) Date of Patent: Mar. 19, 2019

(54) SYSTEMS AND METHODS FOR ADMINISTERING SPINAL CORD STIMULATION BASED ON TEMPORAL PATTERNS OF ELECTRICAL STIMULATION

(71) Applicant: Duke University, Durham, NC (US)

(72) Inventors: Warren M. Grill, Chapel Hill, NC (US); Tianhe Zhang, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/774,156

(22) PCT Filed: Mar. 13, 2014

(86) PCT No.: PCT/US2014/025389
§ 371 (c)(1),
(2) Date: Sep. 10, 2015

(87) PCT Pub. No.: WO2014/159880
PCT Pub. Date: Oct. 2, 2014

(65) Prior Publication Data
US 2016/0038740 A1    Feb. 11, 2016

Related U.S. Application Data

(60) Provisional application No. 61/779,554, filed on Mar. 13, 2013, provisional application No. 61/779,632, filed on Mar. 13, 2013.

(51) Int. Cl.
*A61N 1/36*       (2006.01)
*A61N 1/05*       (2006.01)
(Continued)

(52) U.S. Cl.
CPC ....... *A61N 1/36071* (2013.01); *A61N 1/0551* (2013.01); *A61N 1/36128* (2013.01);
(Continued)

(58) Field of Classification Search
None
See application file for complete search history.

(56) References Cited

U.S. PATENT DOCUMENTS

| 4,338,945 A | 7/1982 | Kosugi et al. |
| 5,716,377 A | 2/1998 | Rise et al. |

(Continued)

FOREIGN PATENT DOCUMENTS

| CN | 102521456 A | 6/2012 |
| JP | 2008506464 A | 3/2008 |

(Continued)

OTHER PUBLICATIONS

Notification of Transmittal of the International Search Report and the Written Opinion of the International Searching Authority or the Declaration, PCT International Searching Authority, dated Aug. 6, 2014.

(Continued)

*Primary Examiner* — Ankit D Tejani
(74) *Attorney, Agent, or Firm* — Olive Law Group, PLLC

(57) ABSTRACT

Systems and methods for administering spinal cord stimulation (SCS) based on temporal patterns of electrical stimulation are disclosed. According to an aspect, a method includes using a computational model of a wide-dynamic range (WDR) neuron to determine one or more non-regular temporal patterns that results in predetermined WDR neuronal output and stimulation activity for one of efficacy optimization and efficiency optimization. The method also includes administering to a subject spinal cord stimulation based on the determined one or more of the non-regular temporal patterns.

26 Claims, 14 Drawing Sheets

(51) Int. Cl.
　　　*G16H 50/50*　　　(2018.01)
　　　*G06F 19/00*　　　(2018.01)
(52) U.S. Cl.
　　　CPC ..... *A61N 1/36171* (2013.01); *A61N 1/36178* (2013.01); *G06F 19/00* (2013.01); *G16H 50/50* (2018.01)

(56) References Cited

U.S. PATENT DOCUMENTS

| | | | |
|---|---|---|---|
| 6,560,490 | B2 | 5/2003 | Grill et al. |
| 6,944,501 | B1 | 9/2005 | Pless |
| 7,191,014 | B2 | 3/2007 | Kobayashi et al. |
| 7,463,927 | B1 | 12/2008 | Chaouat |
| 8,073,544 | B2 | 12/2011 | Pless |
| 2002/0052634 | A1 | 5/2002 | March |
| 2002/0169563 | A1 | 11/2002 | De Carvalho Ferreira |
| 2004/0111127 | A1 | 6/2004 | Gliner |
| 2004/0158298 | A1 | 8/2004 | Gliner et al. |
| 2005/0060009 | A1 | 3/2005 | Goetz |
| 2005/0222641 | A1 | 10/2005 | Pless |
| 2006/0015153 | A1 | 1/2006 | Gliner et al. |
| 2006/0149337 | A1 | 7/2006 | John |
| 2007/0106479 | A1* | 5/2007 | Geerts ............... G09B 23/28 702/19 |
| 2007/0191895 | A1 | 8/2007 | Foreman |
| 2007/0265679 | A1 | 11/2007 | Bradley et al. |
| 2007/0288064 | A1 | 12/2007 | Butson et al. |
| 2008/0046036 | A1* | 2/2008 | King ................ A61N 1/0529 607/59 |
| 2008/0215119 | A1 | 9/2008 | Woods |
| 2009/0204173 | A1 | 8/2009 | Fang et al. |
| 2009/0287271 | A1 | 11/2009 | Blum et al. |
| 2009/0279726 | A1 | 12/2009 | Baskent |
| 2009/0326608 | A1 | 12/2009 | Huynh et al. |
| 2010/0152807 | A1 | 6/2010 | Grill et al. |
| 2010/0191307 | A1 | 7/2010 | Fang et al. |
| 2011/0040351 | A1 | 2/2011 | Butson |
| 2011/0060383 | A1 | 3/2011 | Lineaweaver et al. |
| 2011/0087309 | A1 | 4/2011 | Stypulkowski |
| 2011/0213442 | A1 | 9/2011 | Pless |
| 2012/0136408 | A1 | 5/2012 | Grill et al. |
| 2012/0172946 | A1* | 7/2012 | Alataris ............ A61N 1/36071 607/46 |
| 2012/0253421 | A1 | 10/2012 | Gliner et al. |
| 2013/0006331 | A1 | 1/2013 | Weisgarber et al. |
| 2013/0150922 | A1 | 6/2013 | Butson et al. |
| 2014/0163640 | A1 | 6/2014 | Edgerton et al. |
| 2014/0180361 | A1 | 6/2014 | Burdick et al. |
| 2015/0202446 | A1 | 7/2015 | Franke et al. |

FOREIGN PATENT DOCUMENTS

| | | |
|---|---|---|
| JP | 2011502586 A | 1/2011 |
| JP | 2012-504458 A | 2/2012 |
| WO | 2010/065888 A2 | 6/2010 |

OTHER PUBLICATIONS

Notification of Transmittal of the International Search Report and the Written Opinion of the International Searching Authority, or the Declaration, PCT International Searching Authority, dated Jul. 3, 2014.
Benabid, A., et al, "Long-Term Suppression of Tremor by Chronic Stimulation of the Ventral Intermediate Thalamic Nucleus," Lancet. 337:403-6 (Feb. 16, 1991).
Birdno, M.J., "Analyzing the mechanisms of thalamic deep brain stimulation: computational and clinical studies," Ph.D. Dissertation, Department of Biomedical Engineering, Duke University, Durham, NC, USA (Aug. 2009).
Constantoyannis, C., et al, "Tremor induced by thalamic deep brain stimulation in patients with complex regional face pain," Movement Disorders vol. 19, No. 8, 19:933-936. (2004).
Davis, L., "Handbook of Genetic Algorithms" Van Nostrand Reinhold, NY (1991).
Dorval, A. D., et al., "Deep Brain Stimulation Alleviates Parkinsonian Bradykinesia by Regularizing Thalamic Throughput in Human Subjects,". Society for Neuroscience Abstracts 32. (2007), J Neurophysiol 104: 911-921 (Aug. 2010, First published May 26, 2010).
Feng, X., et al, "Optimal Deep Brain Stimulation of the Subthalamic Nucleus—A Computational Study," J Comput Neurosci. 23(3):265-282 (Jan. 9, 2007).
Final Office Action dated Aug. 10, 2012 in U.S. Appl. No. 12/587,295.
Fogelson, N. et al, "Frequency Dependent Effects of Subthalamic Nucleus Stimulation in Parkinson's Disease," Neuroscience Letters 382:5-9 (2005).
Grefenstette, J.J., "Optimization of Control Parameters for Genetic Algorithms," IEEE Transactions on Systems, Man and Cybernetics 16:122-128 (1986).
Grill, W.M. et al., "Effect of Stimulus Waveform on Tremor Suppression and Paresthesias Evoked by Thalamic Deep Brain Stimulation," Society for Neuroscience Abstracts 29 (2003).
International Search Report and the Written Opinion of the International Searching Authority in corresponding PCT application No. PCT/US09/05459 (dated Dec. 3, 2009).
Kuncel A.M. et al, "Clinical Response to Varying the Stimulus Parameters in Deep Brain Stimulation for Essential Tremor," Movement Disorders 21(11):1920-1928 (2006).
Kupsch, A. et al, "The effects of frequency in pallidal deep brain stimulation for primary dystonia," J Neurol 250:1201-1204 (2003).
Limousin, P. et al, "Effect on Parkinsonian signs and symptoms of bilateral stimulation," The Lancet 345:91-95 (1995).
McIntyre, C.C., et al, "Cellular effects of deep brain stimulation: model-based analysis of activation and inhibition," J Neurophysiol 91:1457-1469 (2004).
Non-Final Office Action dated Mar. 9, 2012 in U.S. Appl. No. 12/587,295.
Notice of Allowance dated Apr. 15, 2013 in U.S. Appl. No. 12/587,295.
Rubin, J.E. et al, "High Frequency Stimulation of the Subthalamic Nucleus Eliminates Pathological Thalamic Rhythmicity in a Computational Model,". J Comput Neurosci 16:211-235 (2004).
Timmerman, L. et al, "The cerebral oscillatory network of parkinsonian resting tremor," Brain, 126:199-212 (2003).
Supplemental European Search Report for European patent application No. EP 14773114, PCT/US2014/025389 dated Nov. 3, 2016.
Extended European Search Report for European patent application No. EP 14773114, dated Oct. 21, 2016.
Extended European Search Report dated Nov. 3, 2016, received in EP Application No. 14776331.2.
Office Action received in U.S. Appl. No. 14/774,160 dated Mar. 24, 2017.
Australian Full Examination Report for Application No. 2014244318 dated Aug. 16, 2017.
International Search Report and Written Opinion for Application No. PCT/US2017/035556 dated Oct. 2, 2017.
U.S. Final Office Action for Application No. 14/774,160 dated Oct. 20, 2017.
European Search Report and Opinion for European Patent Application No. 15814864.3 dated Jan. 8, 2018.
Office Action for Japanese Patent Application No. JP 2016-501841 dated Jan. 9, 2018.
Non-Final Office Action for U.S. Appl. No. 15/321,801 dated Feb. 5, 2018.
Office Action for Japanese Patent Application No. JP 2016-501846 dated Feb. 27, 2018 (six (6) pages).
Australian Examination Report for Application No. 2014244386 dated Jul. 24, 2017.
Non-Final Office Action issued in counterpart U.S. Appl. No. 14/774,160 dated Apr. 6, 2018.
Notice of Acceptance issued in counterpart Australian Application No. 2014244386 dated May 11, 2018 (three (3) pages).
Second Office Action issued in counterpart Japanese Application No. 2016-501841 dated May 15, 2018 with English translation (eighteen (18) pages).

(56) References Cited

OTHER PUBLICATIONS

Australian Examination Report issued in counterpart Australian Application No. 2014244318 dated May 20, 2018 (three (3) pages).
Notice of Allowance issued in counterpart U.S. Appl. No. 15/321,801 dated May 25, 2018.
Decision of Refusal issued in counterpart Japanese Patent Application No. JP 2016-501846 dated Nov. 6, 2018 (four (4) pages).
International Preliminary Report on Patentability and Written Opinion issued in PCT Application No. PCT/US2017/035556 dated Dec. 4, 2018 (eight (8) pages).

* cited by examiner

SYSTEMS AND METHODS FOR ADMINISTERING SPINAL CORD STIMULATION BASED ON TEMPORAL PATTERNS OF ELECTRICAL STIMULATION

CROSS REFERENCE TO RELATED APPLICATIONS

This application is a 35 USC 371 application of PCT International Patent Application No. PCT/US2014/025389, filed Mar. 13, 2014 and titled SYSTEMS AND METHODS FOR ADMINISTERING SPINAL CORD STIMULATION BASED ON TEMPORAL PATTERNS OF ELECTRICAL STIMULATION, which claims priority to U.S. Provisional Patent Application Ser. No. 61/779,554, filed Mar. 13, 2013 and titled SYSTEMS AND METHODS FOR OPTIMIZING SPINAL CORD STIMULATION, and U.S. Provisional Patent Application No. 61/779,632, filed Mar. 13, 2013 and titled SYSTEMS AND METHODS FOR OPTIMIZING SPINAL CORD STIMULATION; all of the contents of which are hereby incorporated by reference herein in their entireties. This application is related to co-owned U.S. patent application Ser. No. 14/774,160, titled SYSTEMS AND METHODS FOR APPLYING ELECTRICAL STIMULATION FOR OPTIMIZING SPINAL CORD STIMULATION, and filed simultaneously.

TECHNICAL FIELD

The presently disclosed subject matter relates to spinal cord stimulation, and more specifically, to administering spinal cord stimulation (SCS) based on temporal patterns of electrical stimulation.

BACKGROUND

SCS has emerged as a viable means of managing chronic pain when kinetic (e.g., physical rehabilitation), pharmaceutical, and surgical therapies have not been effective. However, between 1974 and 1991, according to studies the clinical success of SCS has been highly variable, with a mean of 54.2% and a standard deviation of 20%, and subsequent studies have shown very little improvement. Efforts to improve the clinical efficacy of SCS have focused on the development of more spatially selective electrodes, while only minimal attention has been paid to the temporal patterning of SCS or the effects of SCS on the activity of neurons in the dorsal horn pain processing circuit. Although there have been advances in SCS, there is a continuing need for improved techniques and systems for optimizing SCS.

BRIEF SUMMARY

Systems and methods for administering spinal cord stimulation (SCS) based on temporal patterns of electrical stimulation are disclosed. According to an aspect, a method includes using a computational model of a wide-dynamic range (WDR) neuron to determine one or more non-regular temporal patterns that results in predetermined WDR neuronal output and stimulation activity for one of efficacy optimization and efficiency optimization. The method also includes administering to a subject spinal cord stimulation based on the determined one or more of the non-regular temporal patterns.

BRIEF DESCRIPTION OF THE SEVERAL VIEWS OF THE DRAWINGS

The foregoing aspects and other features of the present subject matter are explained in the following description, taken in connection with the accompanying drawings, wherein.

DETAILED DESCRIPTION

Figure 1:
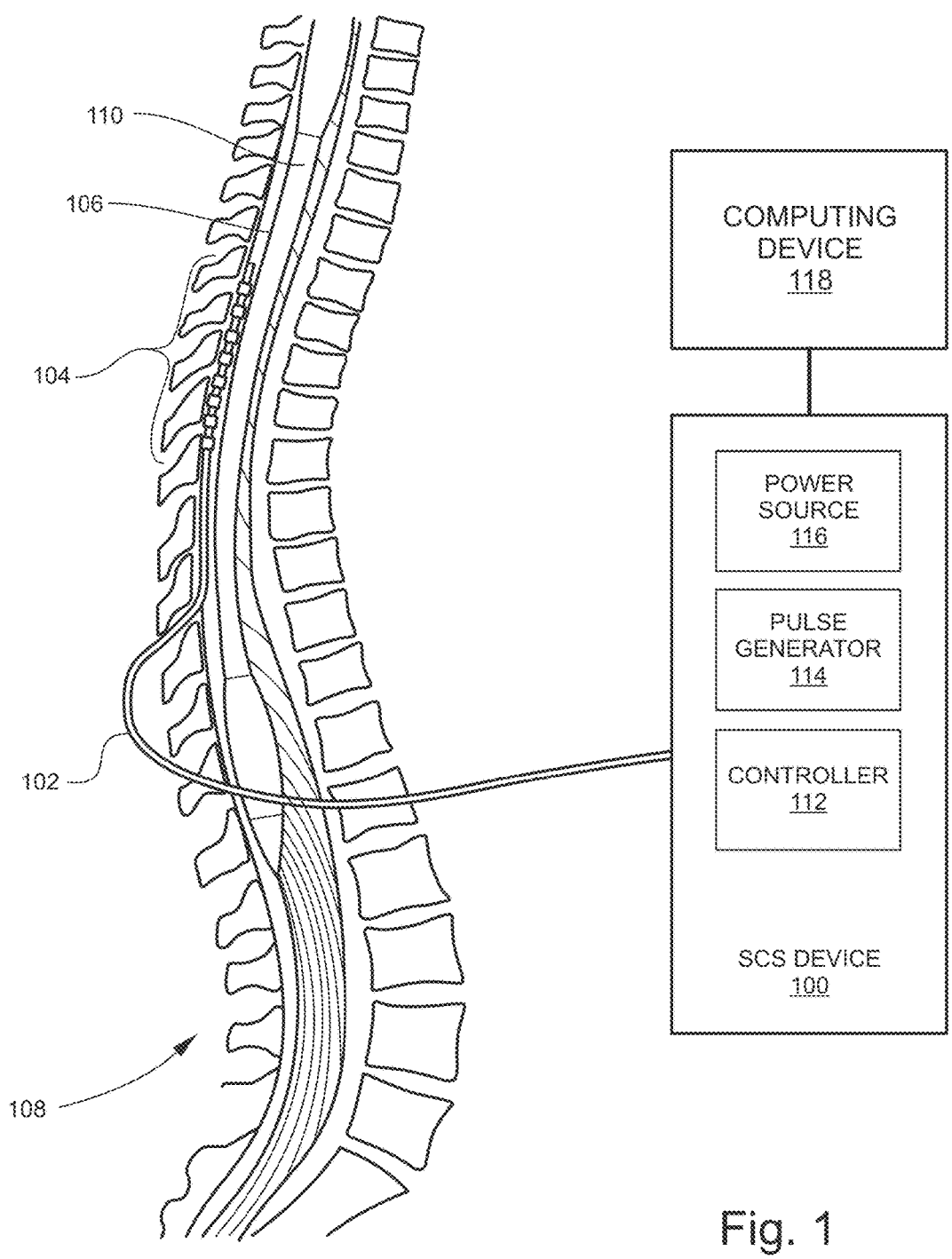
FIG. 1 is an anatomic view of a system for stimulating targeted neurological tissue of a human subject in accordance with embodiments of the present disclosure.

For the purposes of promoting an understanding of the principles of the present disclosure, reference will now be made to various embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

As used herein, the term "subject" and "patient" are used interchangeably herein and refer to both human and non-human animals. The term "non-human animals" of the disclosure includes all vertebrates, e.g., mammals and non-mammals, such as non-human primates, sheep, dog, cat, horse, cow, chickens, amphibians, reptiles, and the like. In examples provided herein, the subject is a human patient in need of spinal cord stimulation.

As used herein, the term "neurological disorder" refers to any pathological condition relating to the brain and/or nervous system. Examples include, but are not limited to, pain, which includes chronic and acute neuropathic pain, migraine, trauma, and the like. As used herein, the term "pain" refers to the basic bodily sensation induced by a noxious stimulus, received by naked nerve endings, characterized by physical discomfort (e.g., pricking, throbbing, aching, etc.) and typically leading to an evasive action by the individual. As used herein, the term pain also includes chronic and acute neuropathic pain. The term "chronic pain" and "chronic neuropathic pain" are used interchangeably refer to a complex, chronic pain state that is usually accompanied by tissue injury wherein the nerve fibers themselves may be damaged, dysfunctional, or injured. These damaged nerve fibers send incorrect signals to other pain centers. The impact of nerve fiber injury includes a change in nerve function both at the site of injury and areas around the injury. Chronic neuropathic pain often seems to have no obvious cause, however, some common causes may include, but are not limited to, alcoholism, amputation, back, leg and hip problems, chemotherapy, diabetes, facial nerve problems, HIV infection or AIDS, multiple sclerosis, shingles, spine injury, and the like. For example, neuropathic pain may include phantom limb syndrome, which occurs when an arm or leg has been removed because of illness or injury, but the brain still gets pain messages from the nerves that originally carried impulses from the missing limb.

As referred to herein, the term "administering" refers to the delivery of an electrical impulse/signal/frequency to a subject to thereby cause stimulation to a nerve, nerve fiber, or group of nerve fibers. For example, electrical impulse/signal/frequency may be applied by use of one or more electrodes in electrical communication with a targeted neurological tissue region, such as sub-populations of dorsal column nerve fibers for example. In other examples, the targeted neurological tissue region may include dorsal roots, dorsal root ganglia, a peripheral nerve, and/or the like.

Unless otherwise defined, all technical terms used herein have the same meaning as commonly understood by one of ordinary skill in the art to which this disclosure belongs.

In accordance with embodiments of the present disclosure, systems and methods of optimizing SCS are disclosed. A system may optimize SCS by using heuristic (genetic algorithm) to optimize the temporal patterning of SCS in such a way as to suppress the transmission of nociceptive information from the spinal cord. In an example, a system may include a pulse generator configured to generate electrical signals for delivery to targeted neurological tissue of a subject. The system may also include one or more SCS electrodes in electrical communication with an output of the pulse generator. The contact(s) may be placed in contact with the targeted neurological tissue. For example, the contact(s) may be placed in electrical communication with one or more sub-populations of dorsal column nerve fibers. A controller of the system may control the pulse generator to administer multiple frequencies of SCS to the electrode contact(s) such that the targeted neurological tissue is stimulated. The system may be configured to generate a stimulation pattern and a cost function. The system may repeat the steps of generating a stimulation pattern and generating a cost function. As an example, the cost function may be fixed or determined by a clinician prior to implantation of an SCS device. Further, the system may select those patterns that have a cost function that favors a combination of low wide-dynamic range (WDR) neuronal output and low stimulation frequency. Subsequent to pattern selection, the controller may generate and administer an optimal SCS based on the selected patterns to thereby suppress the activity of WDR neurons. In some embodiments, the steps are repeated using the generated patterns to thereby provide an optimized pattern. In other embodiments, steps may be continued iteratively until a specified number of generations or a threshold value for the cost function (fitness) of the best (optimal) solution is reached.

FIG. 1 illustrates an anatomic view of a system for stimulating targeted neurological tissue of a human subject in accordance with embodiments of the present disclosure. The subject may be suffering from a neurological disorder, such as chronic pain. Referring to FIG. 1, the system includes an SCS device 100, an electrical cord 102 and an electrode array generally designated 104. The system is shown as being implanted in the subject. Particularly, the electrode array 104 is operatively positioned in the epidural space 106 of a vertebral column 108 of the subject. The electrode array 104 is positioned at the site of nerves that are the target of stimulation, e.g., along the spinal cord 110. Alternatively, the electrode array 104 may be suitably positioned in any other location for desired electrical stimulation of targeted neurological tissue. The cord 102 may include multiple lines or fibers such that different or the same electrical signals can be provided to contacts of the electrode array 104. The SCS device 100 may be suitably implanted within the subject such as, but not limited to, implantation within the abdomen or buttocks. The electrical cord 102 may operatively connect an output of the SCS device 100 to the electrode array 104.

The SCS device 100 may include a controller 112 and a pulse generator 114. The controller 112 may include hardware, software, firmware, or combinations thereof for implementing functionality described herein. For example, the controller 112 may be implemented by one or more processors and memory. The controller 112 may be operatively connected to the pulse generator 114 for controlling the pulse generator 114 to generate electrical signals for applying patterns of electrical stimulation to targeted neurological tissue. The output signals may be received by the electrical cord 102 and carried to the electrode array 104 for electrical stimulation at targeted neurological tissue. The SCS device 100 may include a power source 116, such as a battery, for supplying power to the controller 112 and the pulse generator 114.

The system may also include an external computing device 118 that is not implanted within the subject. The computing device may communicate with the SCS device 100 via any suitable communication link (e.g., a wired, wireless, or optical communication link). The communication link may also facility battery recharge. The computing device 118 may include hardware, software, firmware, or combinations thereof for implementing functionality described herein. For example, the computing device 118 may include one or more processors and memory. A clinician may interact with a user interface of the computing device for programming the output of the implanted pulse generator 114, including the electrodes that are active, the stimulation pulse amplitude, the stimulation pulse duration, the stimulation pattern (including pulse repetition frequency), and the like applied via each electrode contact to each sub-population.

Further, in accordance with embodiments of the present disclosure, the computing device 118 may determine one or more non-regular temporal patterns that results in predetermined WDR neuronal output and stimulation activity. The computing device 118 may communicate information for administering the temporal patterns to the SCS device 100, which may then apply the non-regular temporal pattern(s) of electrical stimulation to targeted neurological tissue of the subject.

A patient may also interact with the user interface of the computing device 118. In this embodiment, the patient may interact with the user interface for selecting among a set of pre-programmed stimulation parameter sets. These sets may have been programmed or otherwise set by the clinician and stored in the controller 112.

Figure 2:
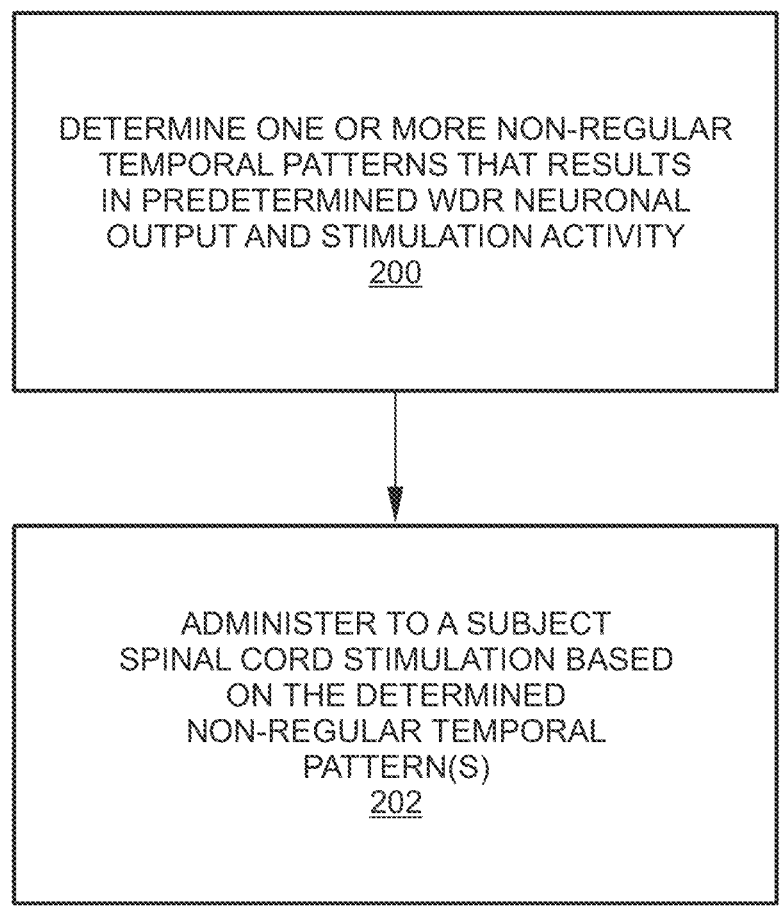
FIG. 2 is a flow chart of an example method for SCS in accordance with embodiments of the present disclosure.

FIG. 2 illustrates a flow chart of an example method for SCS in accordance with embodiments of the present disclosure. The example method is described as being implemented by the system and configuration shown in FIG. 1, although it should be understood that the method may alternatively be implemented by any other suitable system in any other suitable configuration.

Referring to FIG. 2, the method includes determining 204 one or more of the non-regular temporal patterns that results in predetermined WDR neuronal output and stimulation activity. Predetermined WDR neuronal output may include, but is not limited to, the output of a model WDR neuron in a simulation implemented in a computational model, which has inputs for modeling a biological WDR neuron. In this sense, the model WDR neuron's output can be used as a proxy for patient pain (i.e., efficacy). In an example, the computing device 118 may generate and utilize a cost function for optimizing the WDR neuronal output and stimulation activity. Further, the computing device 118 may select one or more of the non-regular temporal patterns based on the cost function. Further, in an example, the computing device 118 may alter the temporal patterns and determine when a threshold value for the cost function is obtained while altering the temporal patterns. Continuing this example, the computing device 118 may determine that the temporal pattern applied when the threshold value is obtained is the non-regular temporal pattern(s) that results in predetermined WDR neuronal output and stimulation activity. This temporal pattern may be determined to be the temporal pattern that provides the lowest WDR neuronal output and the lowest stimulation activity among all other applied temporal patterns. As referred to herein, the term "efficacy" refers to the minimization of model WDR activity (i.e., proxy for reduced pain). As referred to herein, the term "efficiency" refers to a low or the lowest possible device stimulation frequency (i.e., power savings).

In an example of determining temporal patterns, the temporal patterns may be determined by using a search heuristic to determine the patterns that result in the desired WDR neuronal and stimulation activity. The search heuristic may utilize a genetic algorithm, a gradient descent, a simulated annealing technique, and/or the like.

The method of FIG. 2 includes administering 202 to the subject spinal cord stimulation based on the determined one or more of the non-regular temporal patterns. Continuing the aforementioned example, the computing device 118 may communicate to the SCS device 100 the temporal patterns. The controller 112 may control the pulse generator 114 to use the temporal pattern(s) that resulted in the predetermined WDR neuronal output and stimulation activity. This may be the temporal pattern(s) that resulted in the lowest WDR neuronal output and the lowest stimulation activity among all other applied temporal patterns.

In accordance with embodiments, the controller 112 may be configured to control the pulse generator 114 to generate electrical signals that produce non-regular temporal patterns of electrical stimulation to dorsal column nerve fibers. These may be the temporal patterns provided by the computing device 118. One or more contacts of the electrode array 104 may be placed in electrical communication and in position to apply the electrical stimulation to one or more subpopulations of the dorsal column nerve fibers. The pattern of electrical stimulation may be applied at multiple different frequencies and at different timings. Further, for example, the patterns may be applied at different frequencies that are multiples of each other. The pattern of electrical stimulation may include regular temporal patterns of stimulation (i.e., constant interpulse intervals) or non-regular temporal patterns of stimulation (i.e., interpulse intervals that vary in time).

The method of FIG. 2 includes administering 206 to the subject spinal cord stimulation based on the determined one or more of the non-regular temporal patterns. Continuing the aforementioned example, the controller 112 may control the pulse generator 114 to use the temporal pattern(s) that resulted in the predetermined WDR neuronal output and stimulation activity. This may be the temporal pattern(s) that resulted in the lowest WDR neuronal output and the lowest stimulation activity among all other applied temporal patterns.

In accordance with embodiments, a system as disclosed herein may implement an algorithm that controls the delivery of multiple frequencies of SCS through different output channels to different contacts on a SCS electrode. The algorithm may use the output of model dorsal horn WDR projections neurons responsible for transmitting nociceptive information to the brain to optimize the temporal pattern of stimulation delivered during SCS such that stimulation suppresses the activity of these WDR neurons as much as possible and at the lowest possible frequency. For example, the computational model shown in FIG. 4 may be utilized. Further, the relative importance of reducing WDR activity (efficacy) and reducing stimulation frequency (efficiency) can be controlled by modifying the weights on F and S in equation (1) (C=10F+S) to generate a family of optimized stimulation patterns. Optimization occurs using a search heuristic such as a genetic algorithm in which optimal stimulation patterns are developed and evaluated over several iterations, or "generations."

Figure 3:
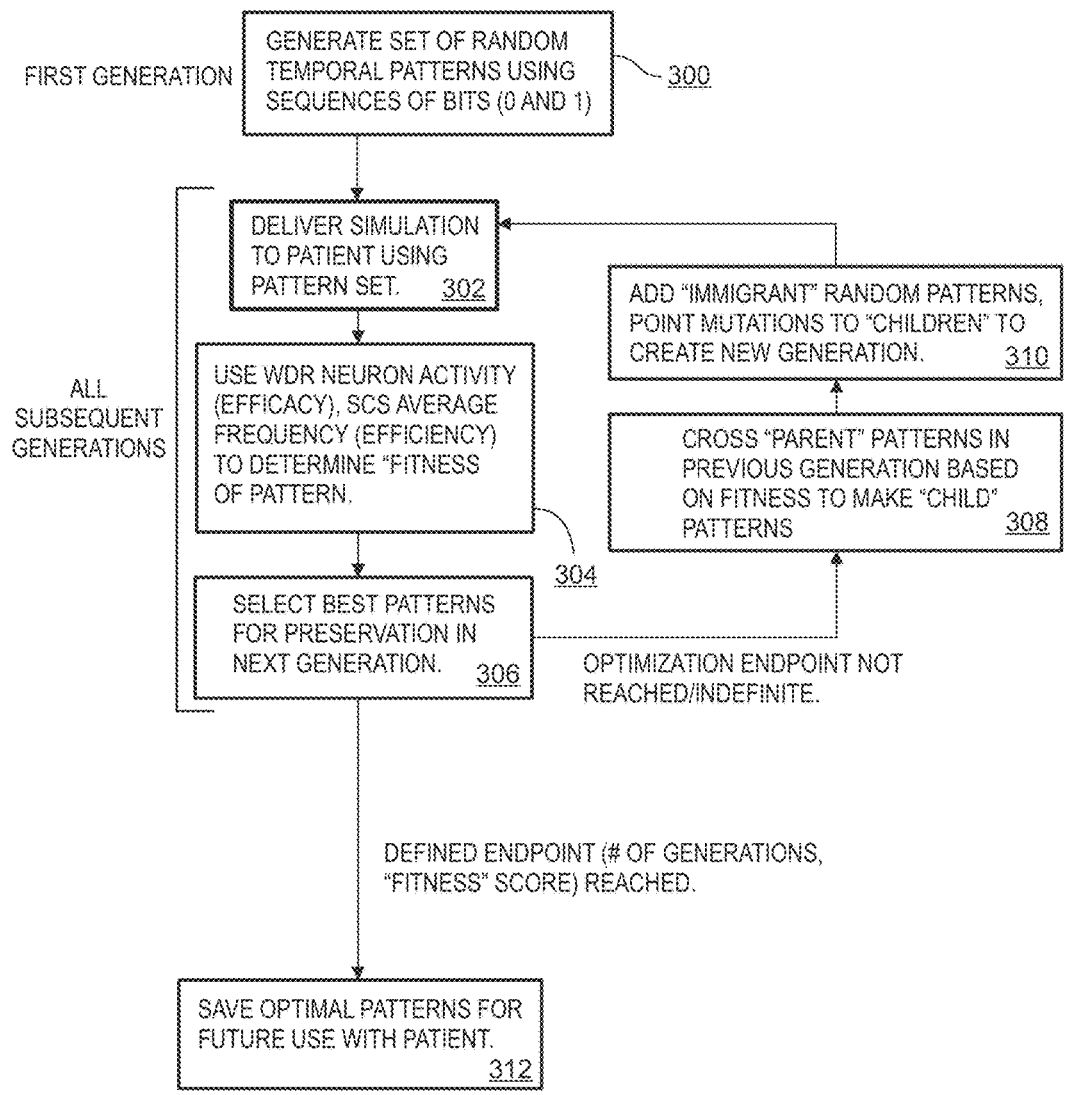
FIG. 3 is a flow chart of an example method of model-based design of optimal temporal patterns of SCS in accordance with embodiments of the present disclosure.

FIG. 3 illustrates a flow chart of an example method of model-based design of optimal temporal patterns of SCS in accordance with embodiments of the present disclosure. The example method may be implemented for example by the computing device 118 shown in FIG. 1, although it should be understood that the method may alternatively be implemented by any other computing device or system. Each stimulation pattern to be tested may be represented as a "gene" comprising a series of bits representing whether stimulation is on or off over the time interval represented by each bit. Referring to FIG. 3, the method includes generating 300 a set of random temporal patterns using sequences of bits (0 and 1).

The method of FIG. 3 also includes delivering 302 stimulation to patient using pattern set. Further, the method includes using 304 WDR neuron activity (efficacy) and SCS average frequency (efficiency) to determine "fitness" of pattern. Stimulation can occur according to the stream of bits represented by each pattern within the set of possible patterns for a previously established period of time, after which the "fitness" of the pattern can be evaluated.

The method of FIG. 3 includes selecting 306 best patterns for preservation in the next generation. Further, the method includes crossing 308 "parent" patterns in the previous generation based on fitness to make "child" patterns, and adding 310 "immigrant" random patterns and point mutations to "children" to create a new generation. Particularly, for example, the best patterns as determined by a cost function that favors a combination of low WDR neuronal output and low stimulation frequency can be kept, and genes of different surviving patterns may be crossed to generate "offspring" patterns for further trials. Further, to introduce variability into the stimulation patterns for the purpose of facilitating convergence to an optimal solution, point mutations may be intermittently applied to the elements in the "offspring" that define the pulse train, and "immigrants" having randomly generated bit sequences (patterns) are interspersed into the population representing the next generation. The method may continue iteratively in the loop of steps 302-310 until a specified number of generations or a threshold value for the cost function (fitness) of the optimal (best) solution is reached. After the optimization is complete, only the stimulation patterns deemed to be most optimal by the algorithm are delivered to the patient. The optimization algorithm may also be toggled on and off (e.g., updates by the physician during check-ups) or set to be on-going with an indefinite endpoint. The method may include saving 312 optimal patterns for future use with a patient.

Figure 4:
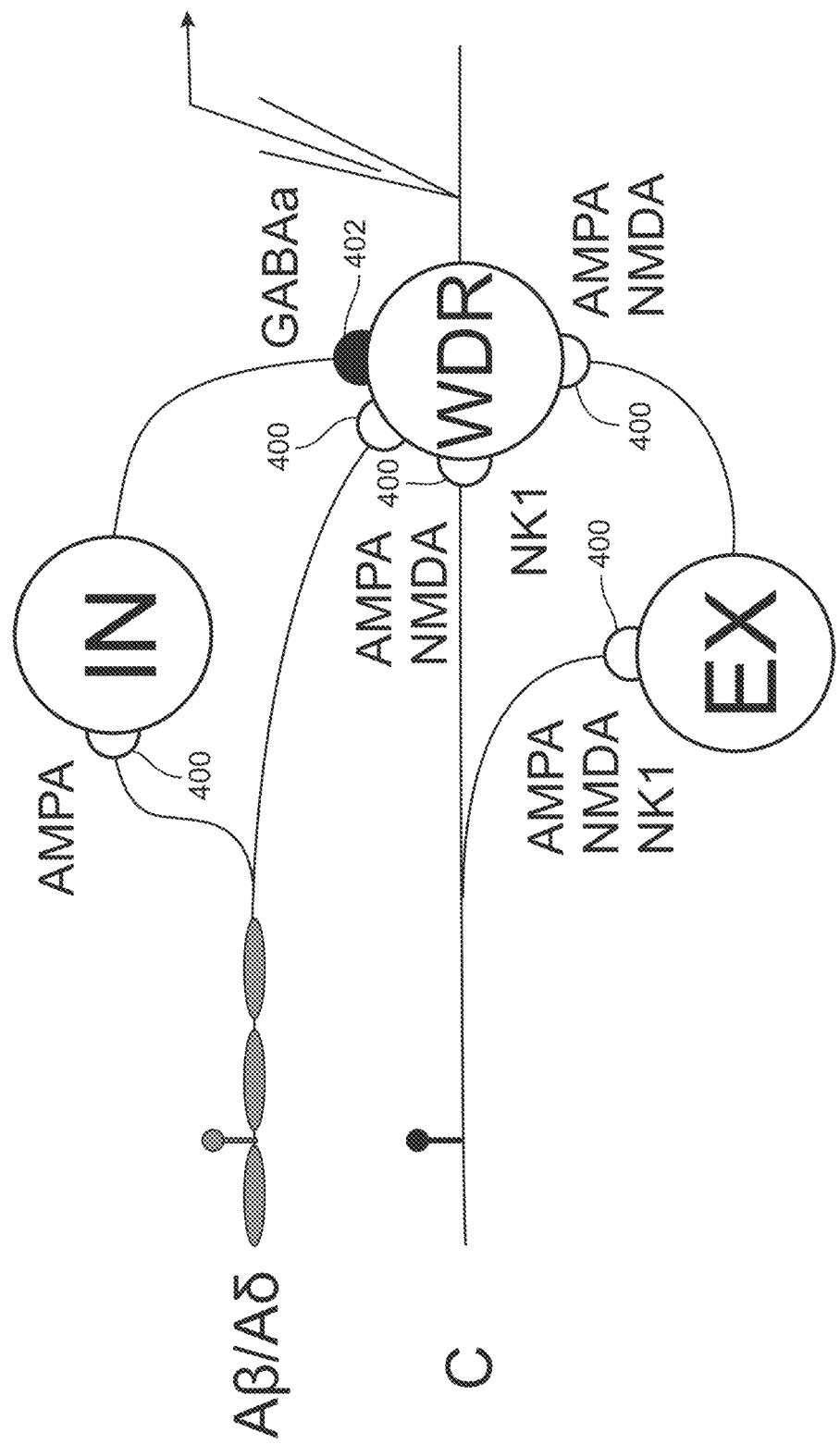
FIG. 4 is a schematic of an example computational model for model-based design and evaluation of optimal temporal patterns of SCS in accordance with embodiments of the present disclosure.

FIG. 4 illustrates a schematic of an example computational model for model-based design and evaluation of optimal temporal patterns of SCS. Referring to FIG. 4, the computational model may include a network of biophysical neurons that are connected to represent a dorsal horn pain processing network. Inputs to the model include 30 A and 30 C primary afferent fibers that convey information from the periphery, and SCS may be delivered to the network via the A fibers to simulate dorsal column fiber activation. Multiple A/C fibers and excitatory interneurons may be used to account for the effect of temporal summation on neuronal activity as well as to add variability to the inputs. In addition, to simulate realistic signal propagation from a peripheral or dorsal column nerve fiber, propagation delays based on the conduction velocities of A and C fibers may be incorporated into all inputs for all simulations. The SCS electrode may be assumed to be 20% of the distance from the dorsal horn network as the peripheral source. In FIG. 4, the "IN" node represents inhibitory interneuron, the "EX" node represents excitatory interneuron, the "WDR" node represents WDR projection neurons. Synapses 400 denote excitatory connections. Synapse 402 denotes an inhibitory connection. SCS using the optimization algorithm may be delivered via the A-fiber input.

Figure 5A:
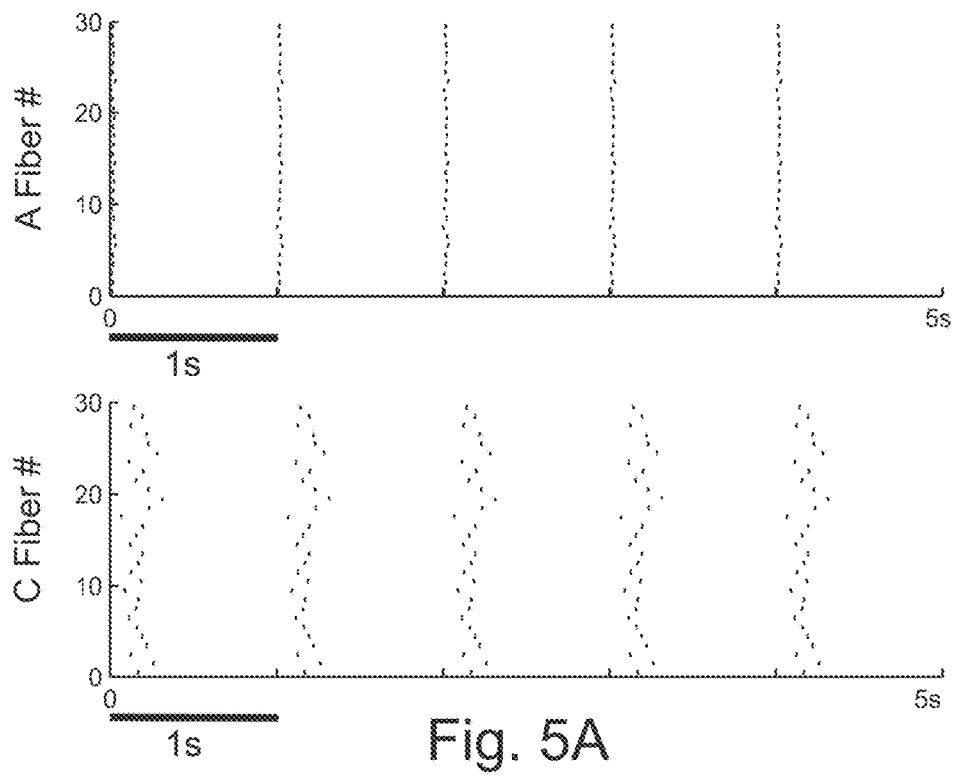
FIGS. 5A and 5B illustrate graphs showing patterns of activity in peripheral primary afferent fibers.
Figure 5B:
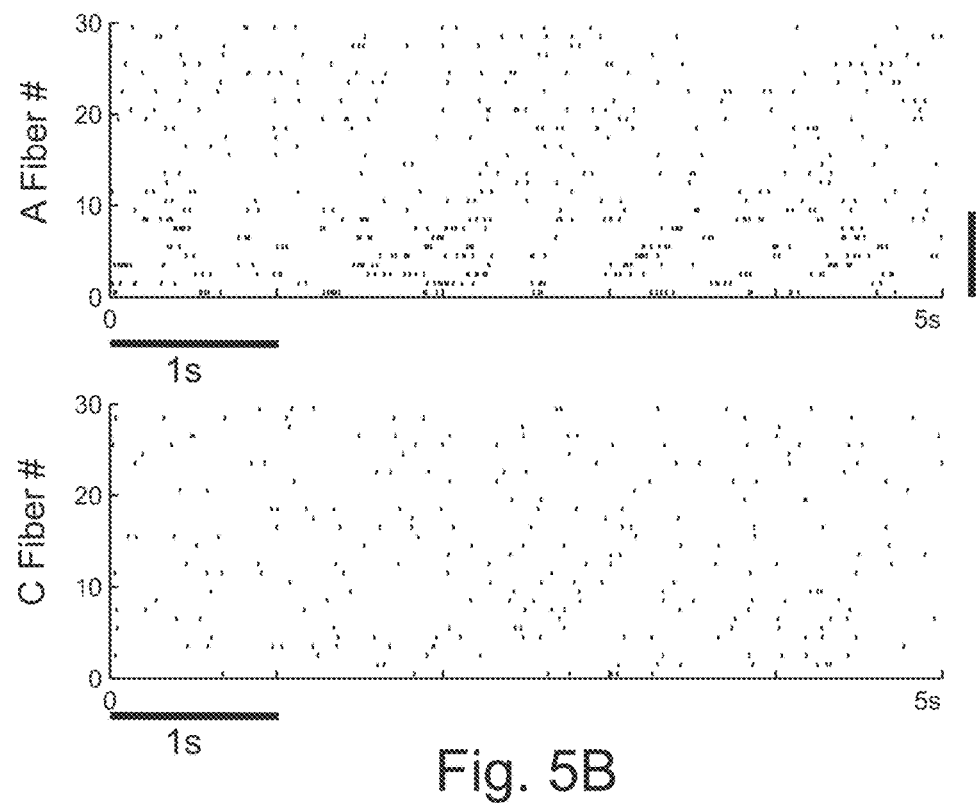
Figure 6:
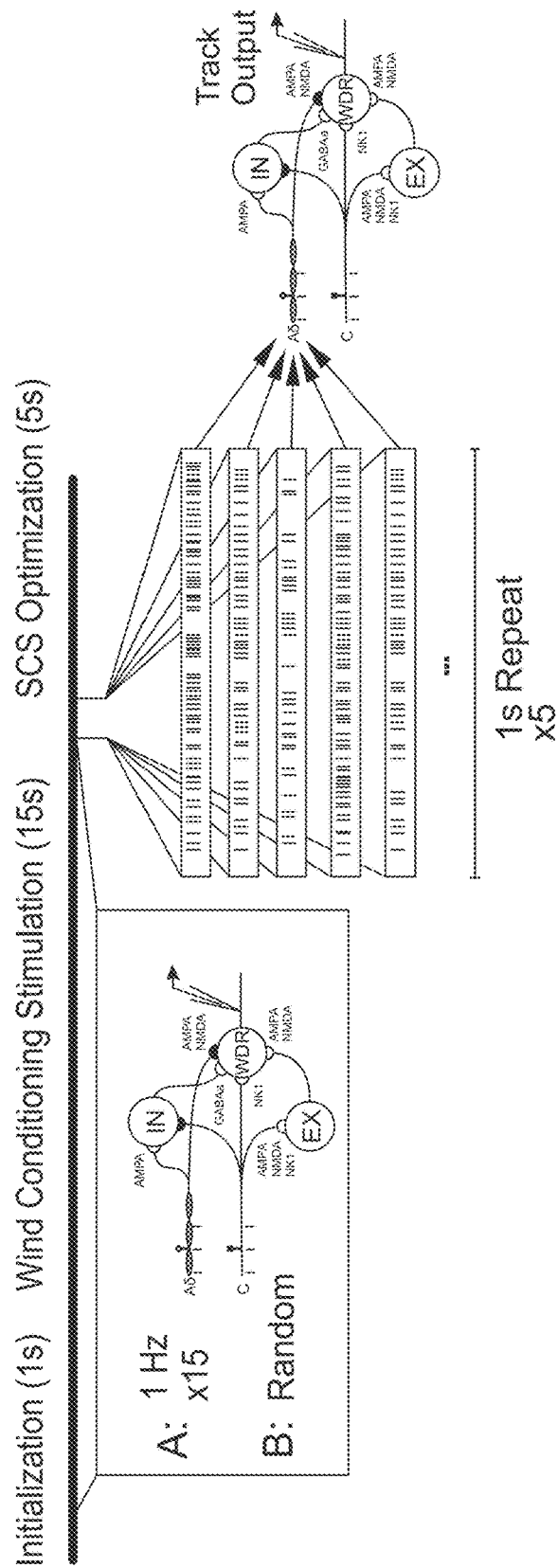
FIG. 6 is a timeline of an example experimental run in accordance with embodiments of the present disclosure.

Computational experiments were conducted as shown in FIG. 6, which illustrates a timeline of an example experimental run. Referring to FIG. 6, SCS may be delivered following a brief model initialization period and 15 seconds of conditioning stimulation using either constant 1 Hz or randomized inputs similar to those recorded from neuromas in live preparations. The output may be tracked and the genetic algorithm may proceed as diagrammed in FIG. 3. More particularly, one second of simulation time was allowed to elapse to allow the model to initialize, and peripheral sensory input including either a constant 1 Hz pulse train synchronized across all fibers or a random spike train based on a Poisson process whose characteristics match those taken from the firing behavior of a peripheral neuroma (See FIGS. 5A and 5B) was then delivered for 15 seconds. FIGS. 5A and 5B illustrate graphs showing patterns of activity in peripheral primary afferent fibers. Representative uniform 1 Hz inputs are shown in FIG. 5A, and randomized inputs representing a neuroma are shown in FIG. 5B. In FIGS. 5A and 5B, a 5-second interval (x-axis) of each is shown for all fiber inputs (y-axis; split by A and C fibers). Each black dot on the graph represents a time point at which a spike is registered by a corresponding input to the model. In FIG. 5B, 30% of the A-fiber inputs exhibit bursting behavior. SCS using 1 second repeats of each temporal stimulation pattern (organism) to be tested within a given generation was delivered for the next 5 seconds while the output of the model WDR neuron was recorded. A set of fixed frequency controls (FFCs) where the output of the WDR neuron in response to and the cost function of constant frequency SCS from 1 Hz to 200 Hz was also run for comparison, as current SCS protocols use fixed frequency stimulation.

The genetic algorithm iterated across 50 generations: the first generation included 25 randomly generated organisms, each containing 1000 "bits" representing 1 millisecond bins during which an SCS pulse may be delivered over a given 1 second interval; the overall SCS pulse train during the 5-second stimulation period was built from 5 successive repeats of a given pattern. The cost function C for each stimulation pattern was determined following each simulation run using a weighted sum of the average frequency of the WDR neuron during the 5-second SCS interval (F) and the average frequency of SCS using the organism (S) as shown in equation (1): $C=10F+S$.

Figure 7A:
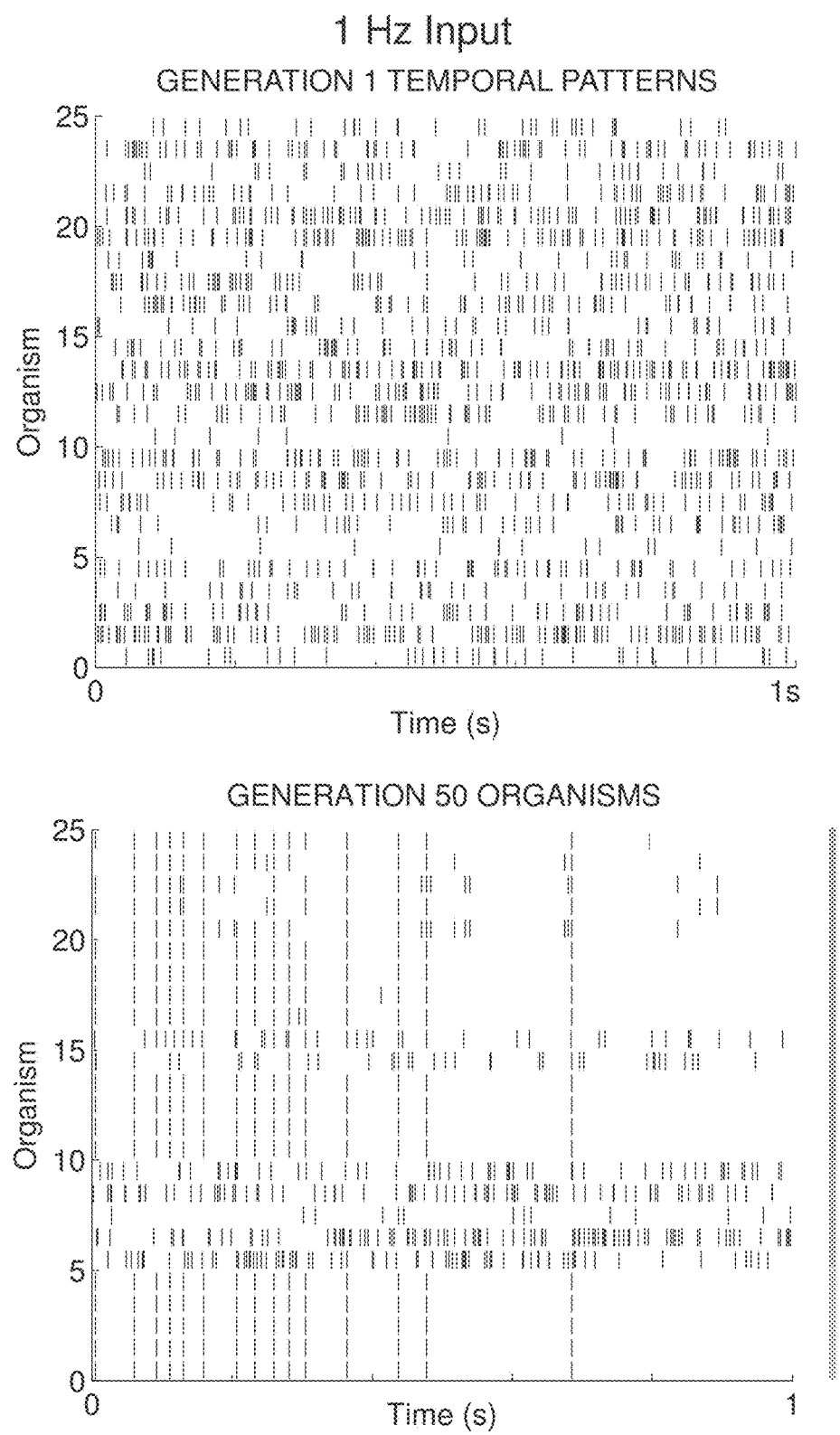
FIG. 7 are plots showing initial and final populations of stimulation patterns used for genetic algorithm-based optimization of SCS in response to a uniform 1 Hz peripheral input and a randomized input resembling that from a neuroma.
Figure 7B:
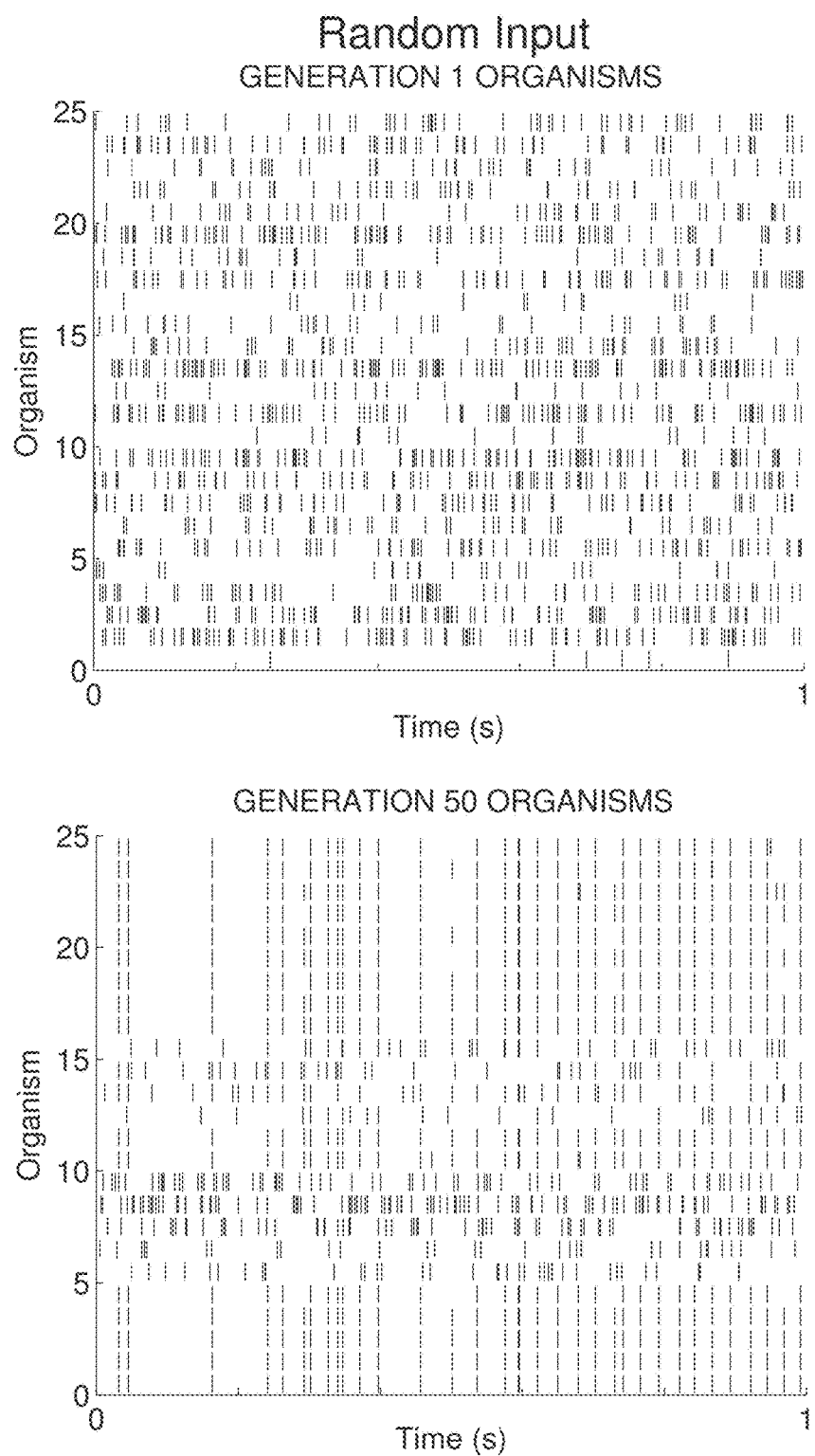

An ideal stimulation train may have a low average frequency while eliciting a minimal WDR neuronal response, so patterns of stimulation yielding lower costs (i.e., minimize C) were deemed more fit. Following the initial fitness evaluation, each subsequent generation was constructed using the 5 most fit (lowest cost function) "survivors" from the previous generation, 5 randomly generated "immigrants," and 15 "children" created from the gene crossings from two organisms (patterns) in the previous generation. Although all patterns in the previous generation may be represented in these offspring, patterns that were more fit had a higher probability of being represented in these crossings than organisms that were less fit. Full populations from generations 1 and 50 demonstrating these principles are shown in FIG. 7, which illustrates plots showing initial and final populations of stimulation patterns used for genetic algorithm-based optimization of SCS in response to a uniform 1 Hz peripheral input (left side of FIG. 7) and a randomized input resembling that from a neuroma (right side of FIG. 7). Referring to FIG. 7, each row is a stimulation pattern, and each black line represents the time point at which a stimulation pulse may be delivered by the stimulator. In the generation 50 population, the line generally designated 700 denotes the most fit survivors (i.e., the patterns with the lowest cost functions) from the previous generation. The line generally designated 702 denotes randomly generated immigrants. Further, the line generally designated 704 denotes the offspring from the crossing of patterns from the previous generation.

Optimization methods in accordance with embodiments of the present disclosure may be used to design unique temporal patterns of SCS that are more effective at suppressing model WDR neuron behavior versus equivalent regular frequency stimulation through testing of the prototype algorithm using a computational model of pain.

Figure 8:
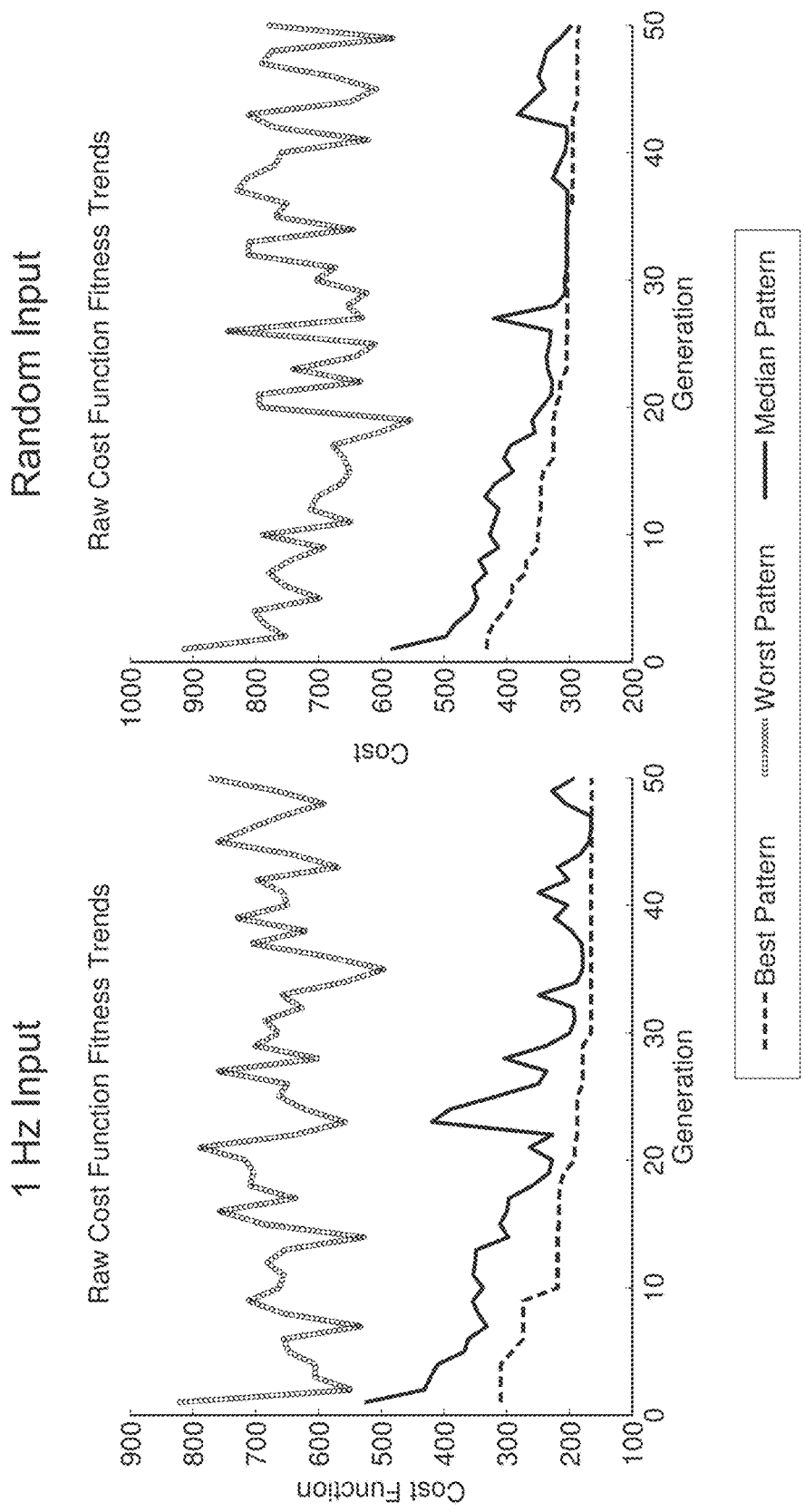
FIG. 8 shows graphs resulting from a 1 Hz peripheral input and a random input.

In accordance with embodiments, over the course of a model-based optimization algorithm, the overall "fitness" of the best pattern for each generation has been shown to improve monotonically when both a non-random and a random peripheral input were applied to the computational model. For example, FIG. 8 shows graphs resulting from a 1 Hz peripheral input and a random input. Particularly, the graphs show the raw cost function scores of the best, median, and worst temporal pattern of stimulation within each generation over the genetic algorithm during a 1 Hz (graph on the left side) and randomized peripheral input (graph on the right side). In the case of the 1 Hz peripheral input, the cost representing the fitness of the best pattern calculated using equation (1) decreased from 309 to 165. In the case of the random peripheral input, the cost representing the fitness of the best pattern calculated using equation (1) decreased from 431 to 285. This decrease in cost underscored a reduction in the firing frequency of the WDR projection neuron in the model from 30.0 Hz to 15.0 Hz in the 1 Hz input case and 40.8 Hz to 25.4 Hz in the random input case during stimulation using the best pattern from the first and last generations, respectively (see FIG. 9). Furthermore, WDR activity during stimulation using the best pattern was consistently suppressed versus a control simulation wherein SCS was not delivered to the computational model both when a 1 Hz and a random peripheral input were delivered. This result indicates that the model-based optimization algorithm is able to generate progressively more effective temporal patterns of SCS relative to a randomly generated initial population.

Figure 9A:
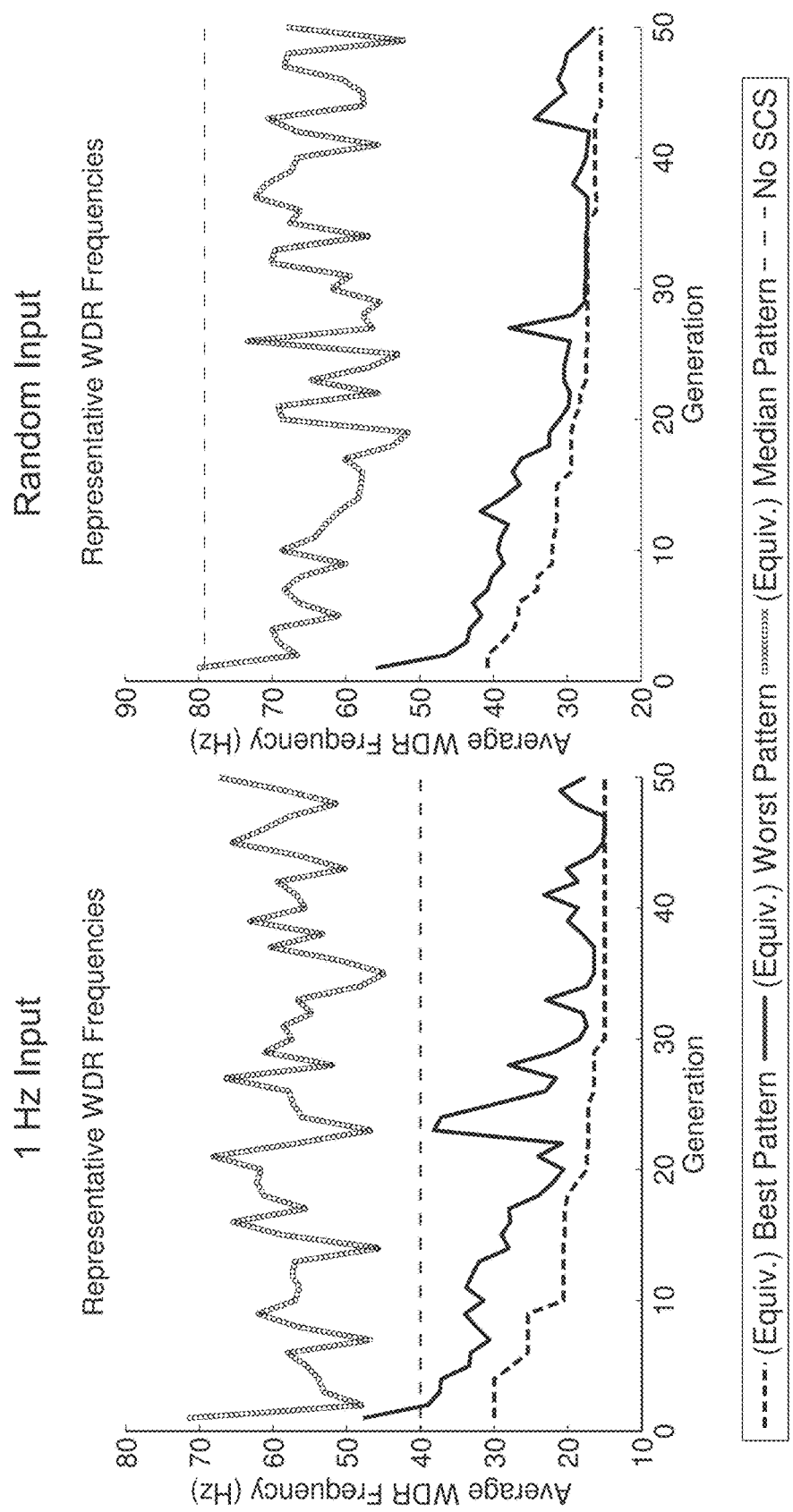
FIG. 9 illustrates graphs showing WDR neuron firing frequencies when the best, median, and worst ranked stimulation patterns and fixed frequency control stimulation at the equivalent frequencies were applied using SCS during a 1 Hz peripheral input and a randomized peripheral input.

FIG. 9 illustrates graphs showing WDR neuron firing frequencies when the best, median, and worst ranked stimulation patterns (top) and fixed frequency control (FFC) stimulation at the equivalent frequencies (bottom) were applied using SCS during a 1 Hz peripheral input (left) and a randomized peripheral input (right). The dotted line represents the average firing frequency of the WDR neuron when no SCS is applied.

Figure 9B:
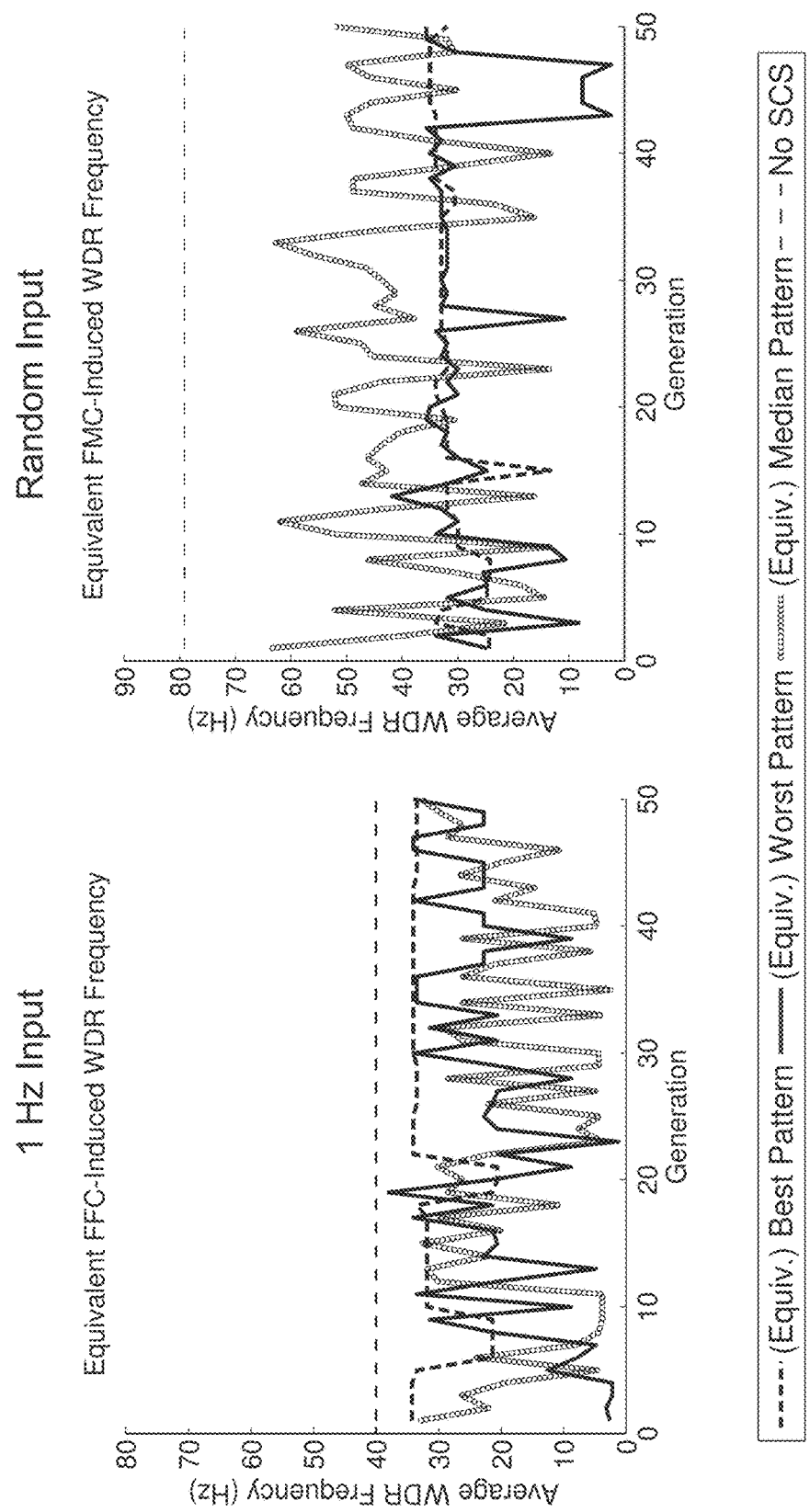
Figure 10:
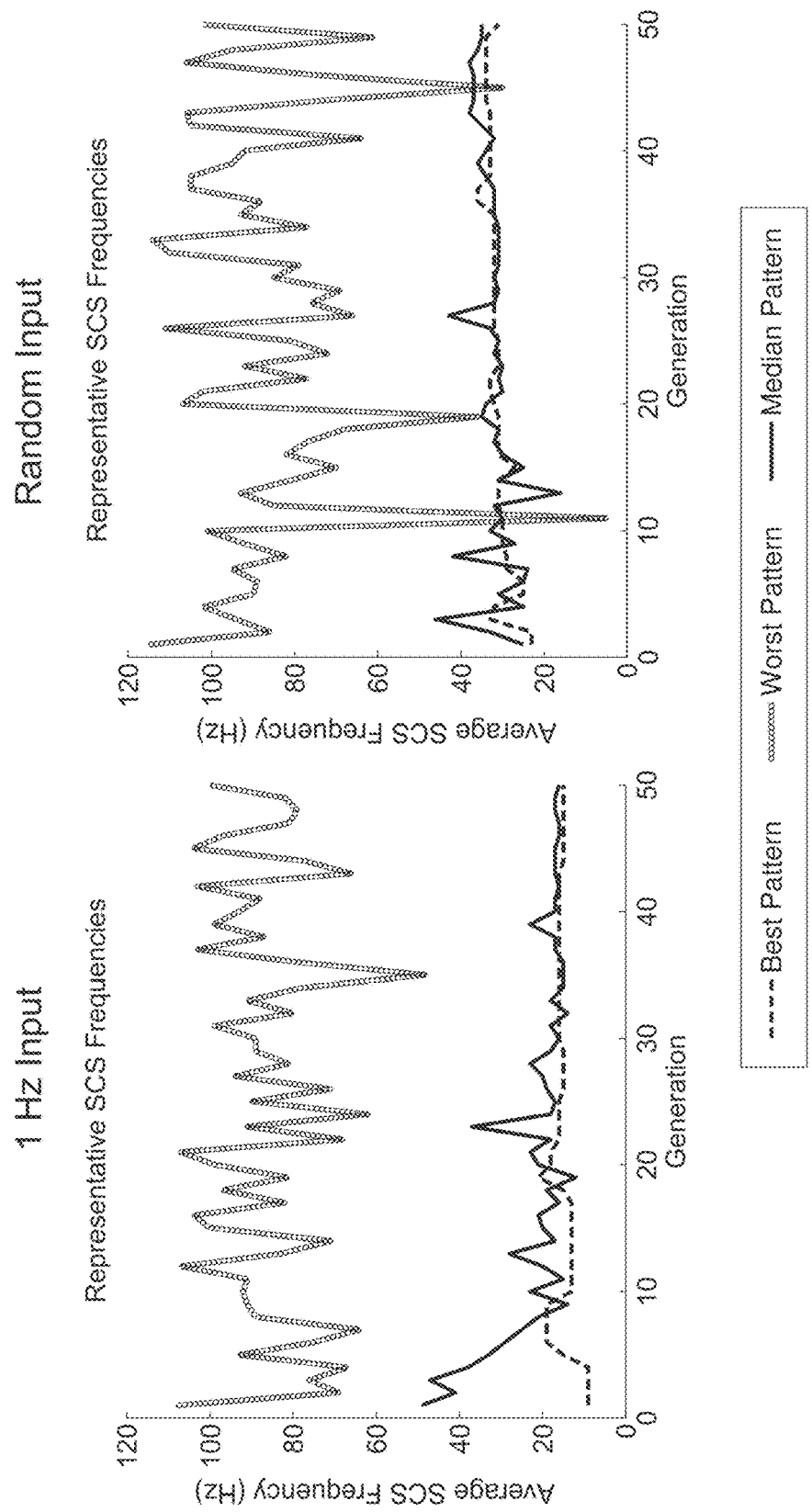
FIG. 10 illustrates graphs showing average stimulation frequencies of the best, median, and worst stimulation patterns in all generations of the genetic algorithm during a 1 Hz peripheral input and a randomized peripheral input.
Figure 11:
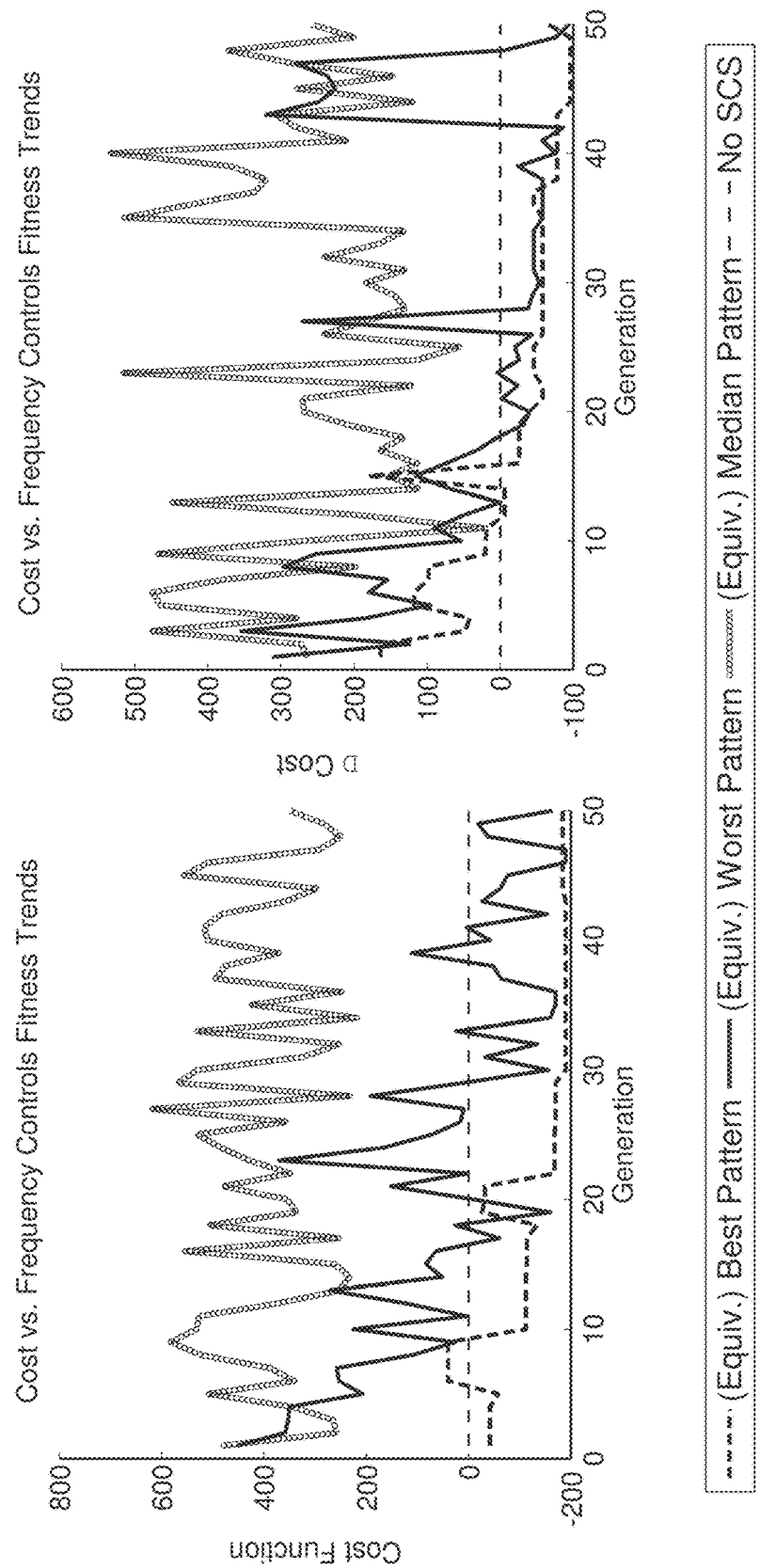
FIG. 11 illustrates graphs showing performance comparisons between the best, median, and worst stimulation patterns in all generations of the genetic algorithm versus equivalent fixed frequency stimulation during a 1 Hz peripheral input and a randomized peripheral input.

The average SCS frequency represented by the best organisms remained relatively constant; the equivalent SCS frequency of the best organism only changed from 9 Hz to 15 Hz during 1 Hz peripheral stimulation and from 23 Hz to 31 Hz during random peripheral stimulation. For example, FIG. 10 illustrates graphs showing average stimulation frequencies of the best, median, and worst stimulation patterns in all generations of the genetic algorithm during a 1 Hz peripheral input (left) and a randomized peripheral input (right). To assess whether the pulse trains generated by the genetic algorithm performed better than equivalent fixed frequency SCS, the fitness of SCS using constant frequency stimulation at the equivalent frequency of the best designed (non-regular) patterns of stimulation was compared with the fitness of the designed patterns themselves. After 50 generations, the best designed patterns for both the regular peripheral stimulation case and the random peripheral stimulation case yielded better performance (lower cost) by equation (1) than their equivalent fixed frequency controls (AC=−184, 1 Hz; AC=−66, random; FIG. 11). As the stimulation frequencies are the same, this improvement in performance (reduction in cost) is due only to greater suppression of WDR neuron activity by the designed patterns (18.4 Hz, 1 Hz; 6.6 Hz, random). The designed patterns at the conclusion of the optimization algorithm are therefore shown to be more effective at suppressing the transmission of nociceptive information than constant frequency stimulation as is used in present-day SCS (FIGS. 9B and 10).

FIG. 11 illustrates graphs showing performance comparisons between the best, median, and worst stimulation patterns in all generations of the genetic algorithm versus equivalent fixed frequency stimulation during a 1 Hz peripheral input (left) and a randomized peripheral input (right). A positive A Cost indicates that fixed frequency stimulation performed better than the stimulation pattern, while a negative A Cost indicates that the stimulation pattern performed better than fixed frequency stimulation.

Figure 12:
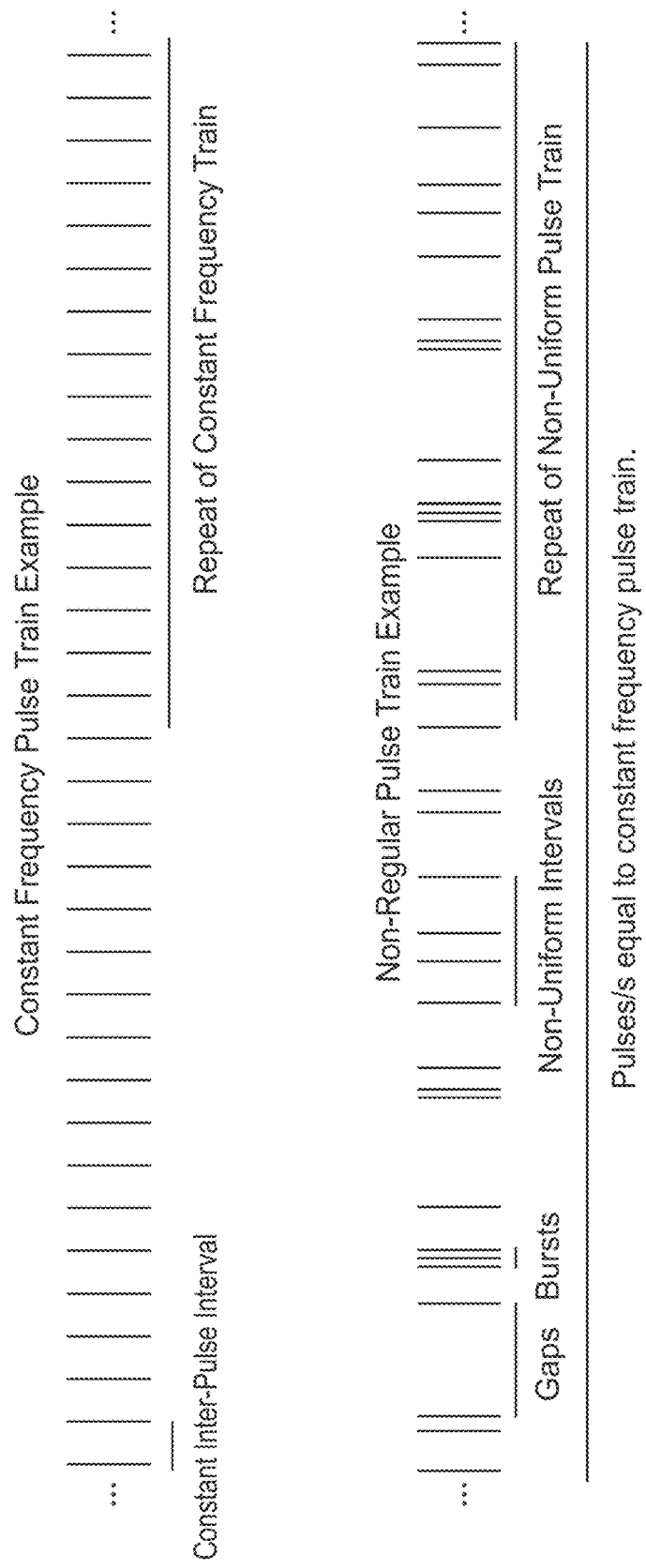
FIG. 12 is an illustration of a regular, constant frequency stimulation train wherein the interpulse intervals are constant in time and examples of non-regular temporal patterns of stimulation wherein the interpulse intervals vary in time.

FIG. 12 illustrates a regular, constant frequency stimulation train wherein the interpulse intervals are constant in time and examples of non-regular temporal patterns of stimulation wherein the interpulse intervals vary in time.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flow chart illustrations and/or block diagrams of methods, apparatus (systems), and computer program products according to embodiments of the subject matter. It will be understood that each block of the flow chart illustrations and/or block diagrams, and combinations of blocks in the flow chart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flow chart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flow chart and/or block diagram block or blocks.

The flow chart and block diagrams in the Figures illustrate the architecture, functionality, and operation of possible implementations of systems, methods, and computer program products according to various embodiments of the present subject matter. In this regard, each block in the flow chart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustration, and combinations of blocks in the block diagrams and/or flow chart illustration, can be implemented by special purpose hardware-based systems that perform the specified functions or acts or carry out combinations of special purpose hardware and computer instructions.

Any patents or publications mentioned in this specification are indicative of the levels of those skilled in the art to which the present subject matter pertains. These patents and publications are herein incorporated by reference to the same extent as if each individual publication was specifically and individually indicated to be incorporated by reference.

One skilled in the art will readily appreciate that the present subject matter is well adapted to carry out the objects and obtain the ends and advantages mentioned, as well as those inherent therein. The present examples along with the methods described herein are presently representative of various embodiments, are exemplary, and are not intended as limitations on the scope of the present subject matter. Changes therein and other uses will occur to those skilled in the art which are encompassed within the spirit of the present subject matter as defined by the scope of the claims.

What is claimed is:

1. A method of identifying an optimized temporal pattern of spinal cord stimulation (SCS), the method comprising:
   generating a plurality of non-regular temporal patterns of SCS using an optimization algorithm based on predetermined performance criteria;
   evaluating the plurality of non-regular temporal patterns of SCS for efficacy optimization using a firing rate or a firing pattern of at least one model neuron within a computational model representing a network of spinal neurons and effects of SCS on the spinal neurons;
   evaluating the plurality of non-regular temporal patterns of SCS for efficiency optimization using average stimulation frequency; and
   identifying at least one candidate non-regular temporal pattern of SCS that results in an optimized firing rate or firing pattern of model neuron activity for efficacy optimization and an optimized stimulation frequency for efficiency optimization.

2. The method of claim 1, wherein identifying the at least one candidate non-regular temporal pattern of SCS comprises selecting the identifying the at least one candidate non-regular temporal pattern of SCS from among other patterns for one of minimizing firing rate of model neuron activity for efficacy optimization and minimizing average stimulation frequency for efficiency optimization.

3. The method of claim 1, comprising using an output of the computational model of a wide dynamic range (WDR) neuron as a measure of model spinal neuron firing rate or firing pattern for efficacy optimization.

4. The method of claim 1, comprising using spinal cord stimulation (SCS) stimulation frequency in the computational model as a proxy for the optimized stimulation frequency for efficiency optimization.

5. The method of claim 4, further comprising generating a cost function for identifying the at least one candidate non-regular temporal pattern of SCS.

6. The method of claim 1, wherein identifying the at least one candidate non-regular temporal pattern of SCS comprises using a search heuristic to determine the at least one candidate non-regular temporal pattern of SCS that results in the optimized firing rate or firing pattern of model neuron activity for efficacy optimization and an optimized stimulation frequency for efficiency optimization.

7. The method of claim 6, wherein using the search heuristic comprises using one of a genetic algorithm, a gradient descent, and a simulated annealing technique.

8. The method of claim 1, wherein the spinal neurons of the computational model comprise wide dynamic range (WDR) neurons.

9. The method of claim 1, further comprising administering to a subject the identified at least one candidate non-regular pattern of SCS.

10. The method of claim 9, wherein administering to a subject comprises applying the identified at least one non-regular temporal pattern to a targeted neurological tissue region of the subject.

11. The method of claim 10, wherein administering to a subject comprises placing at least one electrode in electrical communication with the targeted neurological tissue region for application of the identified at least one candidate non-regular temporal pattern of SCS.

12. The method of claim 10, wherein applying the identified at least one non-regular temporal pattern comprises applying the identified at least one non-regular temporal pattern to at least one sub-population of dorsal column nerve fibers, dorsal roots, dorsal root ganglia, or a peripheral nerve of the subject.

13. The method of claim 10, wherein identifying the at least one candidate non-regular temporal pattern of SCS comprises:
generating a cost function for optimizing spinal neuron firing rate or firing pattern and stimulating output frequency;
tuning the cost function for a pre-determined or patient-specific balance of optimized firing rate or firing pattern of model neuron activity for efficacy optimization and an optimized stimulation frequency for efficiency optimization; and
selecting the at least one candidate non-regular temporal pattern of SCS based on the cost function.

14. The method of claim 13, further comprising:
altering the applied non-regular temporal patterns;
determining when a threshold value for the cost function is obtained while altering the applied non-regular temporal patterns; and
determining that the non-regular temporal pattern applied when the threshold value is obtained is the one or more of the non-regular temporal patterns that results in the optimized firing rate or firing pattern of model neuron activity for efficacy optimization and an optimized stimulation frequency for efficiency optimization.

15. A system of identifying an optimized temporal pattern of spinal cord stimulation (SCS), the system comprising:
at least one processor and memory configured to:
generate a plurality of non-regular temporal patterns of SCS using an optimization algorithm based on pre-determined performance criteria;
evaluate the plurality of non-regular temporal patterns of SCS for efficacy optimization using a firing rate or a firing pattern of at least one model neuron within a computational model representing a network of spinal neurons and effects of SCS on the spinal neurons;
evaluate the plurality of non-regular temporal patterns of SCS for efficiency optimization using average stimulation frequency; and
identify at least one candidate non-regular temporal pattern of SCS that results in an optimized firing rate or firing pattern of model neuron activity for efficacy optimization and an optimized stimulation frequency for efficiency optimization.

16. The system of claim 15, further comprising at least one electrode in electrical communication with a targeted neurological tissue region for application of the identified at least one candidate non-regular temporal pattern of SCS.

17. The system of claim 15, wherein the at least one processor and memory are configured to:
generate a cost function for optimizing a firing rate or a firing pattern of model neuron activity for efficacy optimization and an optimized stimulation frequency for efficiency optimization;
tune the cost function for a pre-determined or patient-specific balance of firing rate or firing pattern of model neuron activity for efficacy optimization and an optimized stimulation frequency for efficiency optimization; and
select the at least one candidate non-regular temporal pattern of SCS based on the cost function.

18. The system of claim 17, wherein the at least one processor and memory are configured to:
alter the applied non-regular temporal patterns;
determine when a threshold value for the cost function is obtained while altering the applied temporal patterns; and
determine that the temporal pattern applied when the threshold value is obtained is the one or more of the non-regular temporal patterns that results in the optimized firing rate or firing pattern of model neuron activity for efficacy optimization and an optimized stimulation frequency for efficiency optimization.

19. The system of claim 15, wherein the at least one processor and memory are configured to use an output of the computational model of a wide dynamic range (WDR) neuron as a measure of the optimized firing rate or firing pattern of model neuron activity for efficacy optimization.

20. The system of claim 15, wherein the at least one processor and memory are configured to use spinal cord stimulation (SCS) stimulation frequency in the computational model as a proxy for the optimized stimulation frequency for efficiency optimization.

21. The system of claim 20, wherein the at least one processor and memory are configured to generate a cost function for selection of the identified at least one candidate non-regular temporal pattern of SCS.

22. The system of claim 15, wherein the at least one processor and memory are configured to use a search heuristic to determine the at least one candidate non-regular temporal pattern of SCS that results in the optimized firing rate or firing pattern of model neuron activity for efficacy optimization and an optimized stimulation frequency for efficiency optimization.

23. The system of claim 22, wherein the search heuristic comprises one of a genetic algorithm, a gradient descent, and a simulated annealing technique.

24. The system of claim 15, wherein the at least one processor and memory are configured to control a pulse generator and one or more electrodes to administer to a subject spinal cord stimulation based on the identified at least one candidate non-regular temporal pattern of SCS.

25. The system of claim 24, further comprising a spinal cord stimulation (SCS) device configured to control the pulse generator and the one or more electrodes to apply the at least one candidate non-regular temporal pattern of SCS to a targeted neurological tissue region of a subject.

26. The system of claim 25, wherein the SCS device is configured to apply the identified at least one candidate non-regular temporal pattern of SCS to at least one subpopulation of dorsal column nerve fibers, dorsal roots, dorsal root ganglia, or a peripheral nerve of the subject.

* * * * *